United States Patent [19]

Piraino et al.

[11] Patent Number: 5,714,464
[45] Date of Patent: Feb. 3, 1998

[54] ANTI-VIRAL MUSHROOM EXTRACTS

[75] Inventors: Frank Piraino, Waunakee; Curtis R. Brandt, Oregon, both of Wis.

[73] Assignee: Wisconsin Alumni Research Foundation, Madison, Wis.

[21] Appl. No.: 468,274

[22] Filed: Aug. 9, 1995

[51] Int. Cl.$^6$ ................................................ C07K 7/02
[52] U.S. Cl. .................. 514/12; 514/14; 530/323; 530/327; 530/345; 530/409
[58] Field of Search .................. 514/12, 14; 530/323, 530/324, 327, 345, 409

[56] References Cited

PUBLICATIONS

Aoki, M., et al., "Antiviral Substances with Systemic Effects Produced by Basidiomycetes such as *Fomes fomentarius*," *Biosci. Biotech. Biochem.*, 57: 278–282 (1993).

Brandt, C.R., et al., "A Murine Model of Herpes Simplex Virus–Induced Ocular Disease for Antiviral Drug Testing," *J. Virol. Methods*, 36: 209–222 (1992).

Driscoll, J., and D. Finley, "A Controlled Breakdown: Antigen Processing and the Turnover of Viral Proteins," *Cell*, 68: 823–825 (1992).

Mayer, R.J., et al., "Ubiquitin in Health and Disease," *Biochimica et Biophysica Acta*, 1089: 141–157 (1991).

Sarkar, S., et al., "Antiviral Effect of the Extract of Culture Medium of *Lentinus edodes* Mycelia on the Replication of Herpes Simplex Virus Type 1," pp. 293–303 (1993).

Sorimachi, K., et al., "Anti–Viral Activity of Water–Solubilized Lignin Derivatives In Vitro," *Agric. Biol. Chem.*, 54:1337–1339 (1990).

Suzuki, H., et al., "Structural Characterization of the Immunoactive and Antiviral Water–Solubilized Lignin in an Extract of the Culture Medium of *Lentinus edodes* Mycelia (LEM)," *Agric. Biol. Chem.*, 54:479–487 (1990).

Tochikura, T.S., et al., "Inhibition (In Vitro) of Replication and of the Cytopathic Effect of Human Immunodeficiency Virus by an Extract of the Culture Medium of *Lentinus edodes* Mycelia," *Med. Microbiol. Immunol.*, 177:235–244 (1988).

*Primary Examiner*—Cecilia J. Tsang
*Assistant Examiner*—Patrick R. Delaney
*Attorney, Agent, or Firm*—Quarles & Brady

[57] ABSTRACT

A substantially pure compound extracted from the mushroom *Rozites caperata* is disclosed. The compound disclosed is SEQ ID NO:1, a twelve amino acid peptide, covalently linked by the epsilon amino group of a carboxy terminal lysine to the carboxyl terminus of SEQ ID NO:2, or a pharmaceutically acceptable nontoxic salt of the compound. The disclosed compound inhibits replication of viruses having lipid bilayer envelopes. Also disclosed is a method for inhibiting replication of viruses having lipid bilayer envelopes. According to the method, such viruses can be inhibited by administering an effective amount of a substantially pure compound, which is SEQ ID NO:1 covalently to SEQ ID NO:2, or a pharmaceutically acceptable nontoxic salt of the compound.

9 Claims, No Drawings

ANTI-VIRAL MUSHROOM EXTRACTS

FIELD OF THE INVENTION

The present invention relates to a compound extracted from the mushroom *Rozites caperata*, which compound inhibits replication of viruses having lipid bilayer envelopes, such as Rous sarcoma virus, herpes simplex virus, varicella zoster, and influenza virus.

BACKGROUND OF THE INVENTION

Medical science has, for decades, used antibiotic agents to treat diseases caused by bacteria or other infectious agents. However, in spite of significant research effort, few agents have been identified with significant activity against viral disease. The search for anti-viral agents has gained immediacy with the emergence of viral diseases (e.g. HIV/AIDS) having fatal consequences. But with few exceptions existing anti-virals are not extensively used in clinical practice either because of unacceptable side effects or disappointing clinical results.

In recent years, research into novel anti-viral compounds has included research on plant products because of the abundance of such products in nature, and also because of their low cytotoxicity in many cases.

Mushrooms have been tested in the past for antibiotic activity against bacteria; only recently has it been realized that some mushrooms also possess anti-viral activity. For example, basidiomycetes such as *Fomes fomentarius* have been found to have systemic effects against plant viruses such as tobacco mosaic virus (TMV). M. Aoki et al, *Biosci. Biotech. Biochem.*, 57(2):278–282, 1993.

In addition, an extract of the edible Japanese mushroom *Lentinus edodes* has been found to have an anti-viral effect on the replication of herpes simplex virus, western equine encephalitis virus, poliovirus, measles virus, and mumps virus. S. Sarka et al, *Anti-Viral Research* 20:293–303, 1993. K. Sorimachi et al., *Agric. Biol. Chem.* 54(5):1337–1339, 1990. *Lentinus edodes* has also been found to inhibit replication of the HIV virus. T. S. Tochikura et al, *Med Microbiol Immunol* 177:235–244, 1988. H. Suzuki et al., *Agric. Biol. Chem.* 54(2):479–487, 1990. Obviously, the need to discover and develop novel chemicals active against viruses is urgent, particularly with the discovery of drug-resistant mutants to Acyclovir, AZT, and amantadine.

SUMMARY OF THE INVENTION

The present invention discloses a substantially pure compound, SEQ ID NO:1, a twelve amino acid peptide, covalently linked by the epsilon amino group of a carboxy terminal lysine to the carboxyl terminus of SEQ ID NO:2, or a pharmaceutically acceptable nontoxic salt of the compound, which compound inhibits replication of viruses having lipid bilayer envelopes. Another embodiment of the present invention discloses a method for inhibiting replication of viruses having lipid bilayer envelopes. According to the method, replication of such viruses can be inhibited by administering an effective amount of a substantially pure compound defined as SEQ ID NO:1 covalently linked by a lysine residue to the carboxyl terminus of SEQ ID NO:2, or a pharmaceutically acceptable nontoxic salt of the compound.

It is an object of the present invention to provide a compound useful in inhibiting replication of viruses having lipid bilayer envelopes, such as Rous sarcoma virus, herpes simplex virus, varicella zoster, and influenza virus.

It is another object of the present invention to provide a method to inhibit replication of viruses having lipid bilayer envelopes, such as Rous sarcoma virus, herpes simplex virus, varicella zoster, and influenza virus.

Other objects, features and advantages of the present invention will become apparent after examination of the specification, claims and drawings.

DETAILED DESCRIPTION OF THE INVENTION

The present invention relates to a compound extracted from the mushroom *Rozites caperata*, which compound inhibits replication of viruses having lipid bilayer envelopes. Such viruses include, for example, Rous sarcoma virus (RSV), herpes simplex virus types 1 and 2 (HSV), varicella zoster, and influenza virus.

The *Rozites caperata* extract has been found to be an effective agent against viral disease both in vitro and in vivo. The effective extract has been analyzed and the active ingredient in the extract has been identified and characterized. The ingredient is a polypeptide made up of two linked proteins. One moiety is a 76 amino acid protein known as ubiquitin. The other protein is a previously unknown 12 amino acid peptide. The carboxyl terminus of the ubiquitin moiety is covalently attached to the epsilon amino group of a lysine residue at the carboxy terminus of the 12-mer.

*Rozites caperata*, easily identifiable by mycologists, is an edible mycorrhizal mushroom in the order Agaricales, the sole number of that genus. The mushroom grows only in association with root systems of coniferous and deciduous trees. As described by Geoffrey Kibby in *Mushrooms and Other Fungi* (page 121), *R. caperata*'s pale ochre cap (2–5 inches in diameter) is finely radially wrinkled and dusted with a fine white frosting of veil at the center. The gills are pale buff and join the stem. The stem is cylindrical, fibrous, and has a white ring around the center and some white fragments with a veil at the base. The spores are rust-brown, 11–14×7–9 .m. roughened. *R. caperata* occurs natively in North America.

The first step in the general strategy used to develop the present invention was to prepare and purify an extract of *R. caperata*. The extract was then characterized as to molecular type and weight, and the extract's activity was tested against several viruses having lipid bilayer envelopes. Such viruses include Rous sarcoma virus, herpes simplex virus types 1 and 2 (HSV), varicella zoster, and influenza virus. Both in vitro and in vivo activity tests were performed. The development of the present invention is described in the examples below.

EXAMPLES

Example 1

Preparation and Purification of Mushroom Extracts

The preparation and purification of *R. caperata* mushroom extracts is outlined in the flow chart presented in Table 1, below.

Specimens of *R. caperata* were identified and provided by Dr. Martyn Dibben of the Milwaukee Public Museum and Dr. Dana Richter of Michigan Technological University, Houghton, Mich. A total of 425 g. of *R. caperata* mushrooms was homogenized in a blender with an equal weight of distilled water at room temperature. The mushroom-water mixture was heated in a water bath at 60° C. for 1.5 hours, then cooled to 22° C. and centrifuged. The water insoluble fraction was discarded; the water soluble extract was harvested and lyophilized. This water soluble fraction was designated as Fraction 1 (see Table 1).

Ammonium Sulfate Precipitation

Pellets of ammonium sulfate salt were added slowly to 18.6 ml of Fraction 1 (having a concentration of 100 mg per ml) while stirring constantly, to achieve a final salt concentration of 61 percent. The mixture was stirred in the cold for two hours, then centrifuged for 15 minutes at 3000 RPM to collect the precipitate and the supernatant. Both the precipitate and the supernatant were dialyzed for two days with six changes of water, two liters per change, until the dialysate tested negative for salt using barium chloride solution. Both the precipitate and the supernatant were lyophized and stored at −70°; they were designated Fractions 2 and 3, respectively; the dialysate was designated Fraction 4.

Molecular Sizing by Gel Filtration.

Fraction 2 was then processed by filtration through an Sephacryl 300 (S 300) column. An S 300 column of dimensions 73×2.5 cm was prepared in distilled water according to the manufacturer's instructions. (Pharmacia). Blue dextran 2000 was used to determine the void volume of 125 mls and the column was standardized using known molecular weight markers. One 10 ml water soluble sample of Fraction 2 was prepared to a concentration of 60 mg/ml and layered on top of the column. This was allowed to percolate through the column by gravity flow, and 6.2 ml fractions were collected in tubes of an LKB 2112 automated fraction collector. The rate of flow was 14 ml per hour. The protein content of each fraction collected was determined by absorption in a spectrophotometer set at 280 mu. Molecular weight calibrations were performed according to the manufacturer's (Pharmacia's) instruction using known protein markers.

Tubes from the two major peaks of absorbance were pooled an designated as Fractions 5 and 6 (see Table 1). Fraction 5 was chromatographed a second time through an S 300 column. Tubes from the two major peaks were pooled and designated as Fractions 7 through 9. The UV spectra were almost identical, with a minimum around 300 λ and maximum at 210–220 λ. These results suggested that the active anti-viral substance or substances have a definite minimum molecular weight in the range of 8–15,000 and may consist of very similar structural compounds.

Acetone Precipitation

For further purification, a 10 percent water soluble solution of designated Fractions 7, 8, 9 were mixed with acetone to a final concentration of 80 percent. The precipitate was allowed to settle for three hours in the cold and then centrifuged at 2500 RPM to harvest the precipitate. The precipitate was air dried and then stored at −20° C. This fraction was further purified by polyacrylamide electrophoresis and used for peptide sequencing.

TABLE 1

Flow Chart of Preparation and Purification Steps
425 grams of wet mushroom, lot 1
60° C., 1.5 hours, Fraction 1
dry weight yield = 7.3%, protein 5.6%
$MID_{100}$ = 1200 μg/ml by CPE in 24-well Vero plates
PAGE - 4 bands MW 90 - 200,000
61% $(NH_4)_2SO_4$

| FR 3 | FR 4 | FR 2 |
|---|---|---|
| supernate | dialysate | precipitate |
| Yield = 1.6% | Yield = 94.6% | Yield = 3.76% |
| | | protein content = 58.5% |
| inactive | inactive | $MID_{100}$ = 80 μg/ml |

TABLE 1-continued

| FR 6 | Sephacryl 300 column FR 5 |
|---|---|
| peak 2, Rav = .57 | peak 1, Rav = .46 |
| M.W = 10-37000 | M.W = 15-40000 |
| $MID_{100}$ = 250 μg/ml | $MID_{100}$ = 30 μg/ml |

| FR 7 | FR 8 | Sephacryl 300 column FR 9 |
|---|---|---|
| peak 1 | peak 2 | peak 2–1 |
| Rav = 0.45 | Rav = 0.60 | Rav = 0.51 |
| nuclear magnetic spectra | | Mass spectrograph M.W = 10427 |

Preparation of HSV-2 Stocks

Herpes simplex virus type 2 (HSV-2, strain 333) was grown on confluent monolayers of Vero cells, a continuous line of African Green Monkey kidneys cells. The virus was harvested when all the cells in the culture showed visual evidence of infection. Cells were frozen and thawed three times, then centrifuged at 3000 RPM to sediment the cells. Supernatant fluids were harvested and titrated for virus content by plaque formation in Vero cells overlaid with Methocel. The plaque forming titers of stocks were routinely of the order of $2 \times 10^7$ plaque forming units per ml/(PFU/ml) Stocks were stored at −70° C. until used.

Tests for Anti-Viral Activity of Purified Fractions.

a. $MID_{100}$ Tests in 24 Well Plates

The effective dose (in μg) of mushroom extract fraction that prevented cytopathic effect (CPE) in 100% of cells (designated as "$MID_{100}$") was used to determine fraction activity; the lower the $MID_{100}$ score, the more active the fraction. Veto cells in medium MEM 10 (Hanks salts minimal essential medium supplemented with 10 percent newborn and calf serum plus penicillin, streptomycin, and fungizone) were trypsinized, resuspended in 100 ml medium, and inoculated into three, 24 well plates; the cells were incubated to cell confluency, usually 2–3 days. After confluency, growth media was removed and cells were infected with 0.1 ml of a 1/100 dilution of virus at 37° C. After one hour, unabsorbed inoculum was removed by suction and replaced with dilutions of the various fractions (in one experiment, an aliquot of Fraction 2 was boiled for 20 minutes at 100° C. and tested for residual anti-viral activity). After three days the cells were tested for anti-vital activity either by inhibition of CPE, or titration of virus yields by plaque formation under methocel overlays (described below). The cells were scored visually for virus cytopathology, rounding and giant cell formation. The sample concentration in wgt/ml which completely prevented cytopathic effect (CPE) in 100% of the cells was calculated (end point assay) to arrive at the $MID_{100}$ per ml of that sample. The results are presented in Table 2.

b. Plaque Forming Units (PFU) per ml

Virus yields of experiments described in part a, above, were determined by plaque formation in Vero cell monolayers overlaid with Methocel. Vero cells were inoculated into six well plates and incubated until confluent. One tenth ml of the virus sample was then inoculated into duplicate wells and infected as described above. After infection Methocel overlays containing medium MEM 10 was then added. Plates were incubated for 5 days and the number of plaques were counted visually under low power magnification. The virus yields are expressed as the number of plaques from cells frozen and thawed three times.

The results are provided in Table 2.

TABLE 2

ANTI-VIRAL ACTIVITY OF FRACTIONS 1-6

| Fraction | MID$_{100}$ µg Sample[1] | Supernatant Virus | Cell Associated Virus Yield Log Reduction[2] |
|---|---|---|---|
| 1 | 1200 | ND | ND |
| 2 | 80 | ND | 4.8 |
| 3 | inactive | | |
| 4 | inactive | | |
| 5 | 30 | ND | ND |
| 6 | 250 | ND | ND |
| 2, 100° 20 min. | 10,000 | | 4.8 |

1. MID$_{100}$=µg sample which prevented CPE in 100% of cells
2. The number of logs$_{10}$ that the virus titer was reduced compared to untreated virus control, titer=$3.7 \times 10^6$ PFU/ml
3. ND—not done In Table 2, Fraction 5 represents a water soluble mushroom extract which was precipitated with 60 percent ammonium sulfate followed by chromatography through a Sephracryl column. This resulted in a 40× increase in the anti-vital potency (compare MID$_{100}$=1200 for Fraction 1, with MID$_{100}$=30 for Fraction 5).

A second filtration through an S 300 column gave essentially the same results as seen in the first filtration. Two peaks of Rav values 0.45 and 0.51 were observed and these were consistent with the two peaks obtained after the first filtration through S 300 of 0.46 and 0.51 respectively. These were fractions designated 7 to 9. Lyophilized samples of Fractions 9 and 7 were analyzed by mass spectroscopy and nuclear magnetic resonance. The NMR result indicated a relatively small protein; the M.S showed a clean sample with a single sharp peak giving a molecular weight of 10427. A second lot of mushrooms of *R. caperata* collected at a different site and date, processed using the same procedure as shown in Table 1, gave a mass spectrograph M.W. of 10,424.

Thus it was clear that the active anti-vital substance was a small heat stable protein of average M.W. 10425.5.

Electroelution and Peptide Sequence of Fractions Isolated in Polyacrylamide Gels.

Protein bands observed after polyacrylamide gel separation were extracted from the gel by using an LKB 2014 Extraphor electrophoretic concentrator, according to the manufacturers instructions. Bands of the appropriate molecular weights were cut from unstained gels, diced into very small pieces and transferred to electroelution chambers. Samples were collected in buffer, lyophilized, resuspended in Mem-10 growth media and tested for anti-vital activity as described. Only a protein migrating with standards between 8,000 and 12,000 daltons was active.

Mass spectroscopy, nuclear magnetic resonance and peptide sequencing of the purified product indicated that the anti-viral principle is a 10.424 KD compound which is a complex of a 12-met (identified as SEQ ID NO:1) covalently bonded to ubiquitin (identified as SEQ ID NO:2), a highly conserved 76 amino acid, heat stable spherical multifunctional 8.560 kd protein.

Sequence Analysis

Purified active material was electrophoresed in a 15% denaturing polyacrylamide gel in accordance with the method described in Balish et al., *J. interferon Res.* 13:289 (1993), and transferred to a PVD filter by electroblotting. The portion of the filter containing the active material was then cut out and subjected to the Edman degradation microsequencing procedure.

Sequence Analysis of the Active Material

Results suggested the active material was proteinaceous. Based on the data revealing that a single component confers the activity (namely NMR, mass spectroscopy, and denaturing polyacrylamide gel electrophoresis), and the known function of ubiquitin, it was concluded that the active material is a protein. The present invention is the first observation that ubiquitin complexes may be used as powerful regulators and inhibitors of vital growth in the treatment and management of viral disease. The active material gave an NMR signal consistent with protein and migrated as a single band on reducing SDS polyacrylamide gels. To identify the material, we determined the amino terminal sequence.

Two amino terminal sequences were obtained. For one component, 21 residues were determined. The sequence of the 21 amino acids were identical to the amino terminus of the protein ubiquitin, indicating that ubiquitin is part of the material. The following 12 amino acid residues were sequenced for the second component: Ala-Asn-Val-Val-Ala-Thr-Tyr-Pro-Ala-His-Ser-Lys. Sequence comparison revealed no known match of this material to any determined protein sequence, suggesting a novel protein was isolated. The 12 amino acid component is identified as SEQ ID NO:1; ubiquitin is identified as SEQ ID NO:2.

It was somewhat surprising to obtain two amino terminal sequences from a single component on a denaturing polyacrylamide gel. However, the identification of ubiquitin as a component provides an explanation for the data.

Ubiquitin is a small molecular weight protein (8.560 dalton) that, as its name implies, is found in all cells, including animals, plants, and fungi. Ubiquitin is highly conserved among species, with only slight variations in the amino acid sequence. Ubiquitin is involved in selective non-lysosomal degradation of proteins, protein processing, antigen recognition and ribosomal stabilization. R. Mayer et al., *Biochimica & Biophysica Acta* 1089:141–157, 1991; J. Driscoll et al., *Cell* 68:823–825, 1992. Ubiquitin functions as a tag or marker for "garbage" collection in the cell. It identifies proteins that have served their useful time or that have been damaged, and targets them for destruction by proteases in the cell. In order to target damaged proteins, the carboxyl terminus of ubiquitin is covalently attached to a lysine residue on the targeted protein. Thus, the protein and ubiquitin become a single molecule. The ubiquitinated protein is then transported to cellular compartments where the ubiquitinated protein is digested, and the ubiquitin itself is freed and recycled.

Example 2

Preparation of *R. Caperata* Extracts

Specimens of *R. caperata* were identified and provided by Dr. Martyn Dibben of the Milwaukee Public Museum. Carpophores were homogenized in Hanks balance salt solution, 50 percent by weight, clarified by centrifugation at 5000 RPM's, and sterilized by filtration through a 0.45 micron millipore filter. The extracts were stored at −70° C.

Viruses Tested

Herpes simplex virus type 1 (HSV-1) strain Macintyre, HSV-2 strain MS, Influenza A strain Shanghai H3N2, obtained from Dr. G. Sedmak, City of Milwaukee Virus Lab, Milwaukee, Wis.; Adenovirus type 6, and enteroviruses Coxsackie A9 and Coxsackie B6 obtained as routine isolates from the Franciscan Shared Labs, Virus Lab, Wauwatosa, Wis.

Cell Lines

The following cell lines were used during these studies: 549 heteroploid human lung cells, normal diploid fibroblast cells MRC-5 and newborn foreskin, were all purchased from Viromed Labs, Minneapolis, Minn. A line of dog kidney cells ("MDCK"), were provided by the City of Milwaukee Virus Lab.

Virus Assays for Anti-viral Activity a. Virus Cytopathic Effects, (CPE) scored from 0–4+.
b. Plaque formation in 549 Cells.
c. Hemadsorption (HAD) and Hemagglutination (HA) assays on MDCK and Cynomolgus monkey cells.

Cytotoxicity of mushroom extracts to cells after exposure for 48–72 hours was secured by ability of cells to exclude 0.50 percent Trypan Blue (TB), and percent viable cell growth compared to untreated controls, (%C).

Cytotoxicity Screening of *R. Caperata* Extracts Against Various Cell Lines Used in These Studies Part a. Culture screw capped tubes of various cells purchased from Viromed Labs were used the day after receipt. Media from duplicate tubes were removed and replaced with a 1/10 dilution of the mushroom extract in Mem-10 media plus two percent chicken embryo allantoic fluid (CEAF) and incubated at 37° C., for 48 hours. Media was removed and cells from two tubes pooled after trypsinization, centrifuged and resuspended in Mem-10 media plus 0.5% trypan blue. Unstained cells were counted in a hemacytometer and results are given in Table 3.

TABLE 3

Cytotoxicity of *R. caperata* for cells after exposure for 48 hours in media Mem-10 plus two percent CEAF Average Viable Cell Count per tube × $10^4$

| | Untreated Control | Treated *R. caperata* | Percent Control |
|---|---|---|---|
| Cynomolgus monkey kidney cells | 128 | 108 | 84 |
| Newborn foreskin fibroblasts | 33 | 39 | 118 |
| MRC-5 diploid lung | 51 | 51 | 100 |
| 549 heteroploid lung | 151 | 136 | 90 |

Part b. Cytotoxicity Tests on MDCK Cells

Test 1. One 75 cm flask of MDCK cells were trypsinized, resuspended in media MEM-10, and 250,000 were inoculated in 24 well Costar plates. The next day triplicate wells were exposed to doubling dilutions of *R. caperata*. After three days' incubation at 37° C., cells from triplicate wells were trypsinized, pooled, and resuspended in MEM-10 plus 0.5% TB and counted in a hemacytometer chamber. Results are given in Table 4.

TABLE 4

Percent Viability and Viable Cell Counts of MDCK Cells after three days' incubation with *R. caperata* extracts diluted 1/10–1/160

| Diln. *R. caperata* | Percent Viability | Viable Cell Count × $10^4$ |
|---|---|---|
| Cell Control | 99.2 | 123 |
| 10 | 94.3 | 105 |
| 20 | 95.7 | 114 |
| 40 | 96.9 | 160 |
| 80 | 95.9 | 166 |
| 160 | 95.1 | 146 |

Test 2. Cytotoxicity Study of *R. caperata* extract's effects on growth of MDCK cells from low density to high density. Doubling dilutions of *R. caperata* were made in MEM-10 media. One ml of *R. caperata* media was then delivered into triplicate wells of 24 well Costar plates. Then 250,000 MDCK cells were added per cell and the plates were incubated at 37° C., for two days. Media were then removed and the cells trypsinized and resuspended in TB counting media. The results are given in Table 5.

TABLE 5

Cell Yields of MDCK Cells Grown in the Presence of *R. Caperata* Extracts

| Treatment | Percent Viability | Average Viable Cell Count per well × $10^4$ | Percent Control | Yield |
|---|---|---|---|---|
| None | 100 | 150 | 100 | 9x |
| 1/5 | 100 | 92 | 61 | 3x |
| 1/10 | 100 | 96 | 64 | 4x |
| 1/20 | 100 | 95 | 63 | 4x |
| 1/40 | 100 | 90 | 60 | 3x |

We concluded that under conditions of anti-viral tests *R. caperata* is not cytotoxic; however the crude extracts appear to be cytostatic for growing MCDK cultures.

Anti-Viral Activity of *R. Caperata* Against HSV-2

One 75 cm T flask of confluent 549 cells was trypsinized and cells were diluted in Medium MEM plus 10 percent fetal calf serum (MEM-10). The cells were distributed into two 24 well Costar plates and incubated overnight at 37° C. in a CO2 incubator. The next day the medium was removed and each well was inoculated with 0.1 ml of a 1/1000 dilution of HSV-2 with a plaque titer of about one million plaque forming units, (PFU)/ml. Virus was absorbed for one hour at 37° C., the cells washed once with MEM-10, and the media replaced with mushroom extracts added from dilutions of 1/10–1/40 in medium MEM-10 plus 10 percent CEAF. After 48 hours the cells were scored for CPE and fluids were removed and titrated for plaque titers on 549 cells under nutrient agar after another 48 hours. Concurrently, 549 cells exposed to mushroom extracts were collected by trypsinization, resuspended in medium MEM-10 plus TB, and counted in a haemocytometer chamber for cell viability. The results, given in Table 6, show that a 1/10 dilution of the mushroom extract showed definite anti-vital activity against HSV-2.

TABLE 6

Anti-Viral Activity of *R. Caperata* Against HSV-2 in 549 Cells

| a. | Virus CPE | Time after Virus Infection | (Hours) |
|---|---|---|---|
| | | 24 | 48 |
| | Diln. *R. caperata* virus control | 4+ | 4+ |
| | 1/10 | 0 | 0 |
| | 1/20 | 1+ | 4+ |
| | 1/40 | 1+ | 4+ |

| b. | Virus Yields (48 hrs) | P.F.U./ml | Yield |
|---|---|---|---|
| | virus control | 5 × $10^6$ | 1.00 |
| | 1/10 | 2 × $10^2$ | .004 | c. Cytotoxicity by TB Dye Exclusion and Cell Yields After 48 hours.

| | Percent Viability | Average No. Cells/well | % C |
|---|---|---|---|
| Untreated Cells | 100 | 570,000 | 100 |
| 1/10 diln. *R. caperata* | 100 | 400,000 | 70 |

Anti-Viral Activity of *R. Caperata* Against HSV-1 in Cynomolgus Monkey Kidney Cells Two tubes each of Cynomolgus monkey cells were infected with 0.1 mls of 1/100 dilution of HSV-1 (titer five million PFU/ml). Virus was absorbed for one hour at 37° C., and cells were washed three times with medium MEM-10 to remove unabsorbed virus. *R. caperata* was added at a diln. of 1/10 in Medium MEM-10 and tubes were incubated for up to 84 hours at 37° C. Virus supernatants were harvested at various time periods and tested for plaque formation on 549 cells. Control cells were examined for cytotoxic effects for four days and none was observed. The results are given in Table 7, and show that the mushroom extract significantly reduced HSV-1 activity.

TABLE 7

Anti-Viral Effect of *R. Caperata* on HSV-1 in Cynomolgus Monkey Kidney Cells Virus Yields (PFU/ml)

| Time After Infection | Infected Control | R. caperata treated | Ratio treated/control |
|---|---|---|---|
| 0 hrs | 460 | 715 | 1.6 |
| 12 hrs | 200 | 30 | 0.15 |
| 36 hrs | 5,000 | 15 | .003 |
| 84 hrs | 253,000 | 7,650 | .030 |

Anti-Viral Activity of *R. Caperata* Extracts Against Influenza Virus Type A, Shanghai H3N2 in MDCK Canine Kidney Cells, (See Tables 8, 9) and Cynomolgus Monkey Kidney Cells, (see Table 10)

Each well of a 24 well Costar plate was inoculated with 250,000 MDCK cells in medium MEM-10 and incubated at 37° C., for four days. At that time, growth medium was discarded and cells infected with 0.1 ml of ten fold dilutions of Influenza virus A, Shanghai incubated at 37° C., for one hour. Cells were washed once with MEM-2, to remove unabsorbed virus and the medium was replaced with 1 ml of a 1/10 dilution of *R. caperata*. After two days supernatants were removed and cells were scored for vital CPE and ability of infected cells to bind guinea pig erythrocytes, (viral haemadsorption). Both viral activities were scored from a maximum of 4+ to 0. These results, provided in Table 8, show that the mushroom extract definitely inhibited replication of the influenza virus.

TABLE 8

Inhibition of Influenza A, Shanghai, by 1/10 Dilution of *R. Caperata* in MDCK Cells

| Virus dose | Infected CPE | Control HAD | R. caperata CPE | Treated HAD |
|---|---|---|---|---|
| undiluted | 4+ | 4+ | 1+ | 2+ |
| 1/10 | 4+ | 4+ | 0 | 1+ |
| 1/100 | 1+ | 4+ | 0 | +/− |
| 1/1000 | 0 | 4+ | 0 | 0 |

In another test 250,000 MDCK suspended in medium MEM-10 were inoculated into each well of 24 well Costar plates and incubated for two days at 37° C. Growth media was removed and cells were infected with 0.1 ml of ten fold dilutions of Shanghai A virus diluted in MEM plus 10 percent bovine serum albumin, for one hour at 37° C. Unabsorbed virus was removed by washing and the media was replaced with doubling dilutions of caperata in Medium MEM plus 10 percent bovine serum albumin. The plate was then incubated for an additional three days. Supernatant fluids were removed and titrated for virus activity by hemagglutination of guinea pig red blood cells. The results, provided in Table 9, show that the mushroom extract definitely inhibited replication of the Shanghai virus.

TABLE 9

Inhibition of Shanghai Influenza Virus A by Diluted Extracts of *R. Caperata* in Medium MEM Plus 10 Percent Bovine Serum Albumin in MDCK Cells

| | Dilution of R. Caperata and HA Titers | | | |
|---|---|---|---|---|
| Virus dose | None | 40 | 80 | 160 |
| 1/10 | 10 | 5 | 5 | 5 |
| 1/100 | 10 | 0 | 5 | 5 |
| 1/1000 | 5 | 0 | 0 | 5 |

Duplicate culture tubes of Cynomolgus monkey cells were pretreated for one day with a 1/10 dilution of *R. caperata* extract in medium MEM 2 plus two percent fetal bovine serum. Then the fluids were removed and saved. Cells were then infected with 0.1 ml of undiluted Shanghai virus, (Titer=320 HA units/ml chicken allantoic fluid; After one hour, the cells were washed thrice and *R. caperata* media returned to the appropriate tubes. These were then incubated for an additional three days at 37° C. The fluids were then harvested and tested for HA activity. These results are given in Table 10, showing the mushroom extract had an anti-vital effect against Shanghai virus.

TABLE 10

Anti-Viral Activity of *R. Caperata* Extracts Against Shanghai Virus in Cynomolgus Monkey Kidney Cells

| Viral Activity | Infected Control | R. Caperata Treated |
|---|---|---|
| Viral CPE | 4+ | 2+ |
| HA Titer | 32 | 4 |

Anti-Viral Activity Against Other Viruses

Crude undiluted *R. caperata* extract was dialyzed against Hanks balanced salt solution for two days at room temperature. The extract was then sterilized by filtration. Duplicate wells of a 24 well Costar plate were inoculated with 549 cells and used two days later. Uninfected cells were treated with doubling of extract and held for five days at 37° C. The cells were then tested for viability and cell growth as described earlier.

The results of cytotoxicity tests are set forth in Table 11. The results of tests of the anti-viral activity of dialyzed extract against HSV-2, V. Zoster, Adenovirus, and the enteroviruses Coxsackie B5 and Coxsackie A9, are collected in Table 12. Table 13 summarizes the results of the activity of *R. caperata* extract against all tested viruses.

TABLE 11

Cytoxicity of Dialyzed *R. Caperata* Extract for 549 Cells After Five Days

| Diln R. caperata | % Viability (TB) | Avg. No. Cells per well/$10^4$ |
|---|---|---|
| 1/5 | 100 | 45 |
| 1/10 | 100 | 50 |
| 1/20 | 100 | 42 |

TABLE 12

Anti-Viral Activity of 1/5 Dilution of R. Caperata Extract
in Various Infected Cell Lines After Three Days

| Virus | Cell Line | Cytopathogenicity Infected Control | Mushroom Treated |
|---|---|---|---|
| HSV-2 | Foreskin | 4+ | 0 |
| V. Zoster | 549 | 58 | 0 |
| Adenovirus | Vero | 4+ | 4+ |
| Coxsackie B5 | HEP-2 | 4+ | 4+ |
| Coxsackie A9 | MRC-5 | 4+ | 4+ |

TABLE 13

Summary of R. Caperata Extract Anti-Viral Activity

| Virus Tested | Sensitive or Resistant |
|---|---|
| HSV-1 | Sensitive |
| HSV-2 | Sensitive |
| Varicella zoster | Sensitive |
| Influenza A Shanghai | Sensitive |
| Rous Sarcoma Virus | Sensitive |
| Adenovirus | Resistant |
| Coxsackie A9 | Resistant |
| Coxsackie B5 | Resistant |

The studies represented by the results summarized in Table 13 show that the mushroom extract has significant anti-viral activity against viruses having lipid bilayer envelopes, such as those listed in Table as showing a sensitivity to the extract. However, viruses which do not have lipid bilayer envelopes, such as adenovirus and the enteroviruses, are resistant to the extract.

Example 3

IN VIVO EXPERIMENTS

Mushroom Extract

The active R. caperata mushroom extract was prepared as described in Example 2. For use in vivo, it was suspended in 50 mM sodium acetate (pH 7.0).

Virus

HSV-1 strain KOS, which causes severe stromal keratitis, was used for all studies. High Titer stocks were prepared in Vero cells as we have described in Example 2, according to the method of Grau et al., Invest. Opthalmol. Vis. Sci., 30:2474 (1989).

Animal Infection and Disease Scoring

Mice, 5–6 week old BALB/c females, were anesthetized using 5% halothane. The right cornea was scarified using a 30 ga. needle, and a 5 µl drop of media (DME with 2% serum) containing $1 \times 10^5$ plaque forming units of HSV-1 KOS was placed on the cornea. After 20–30 seconds, the excess was removed with a swab and the mouse returned to its cage. The severity of ocular disease was then scored at various times. Blepharitis (eyelid inflammation and conjunctivitis), vascularization (blood vessels in the cornea), and stromal keratitis (corneal clouding) were scored as described in Brandt et al., "A Murine Model of Herpes Simplex Virus-Induced Ocular Disease for Antiviral Drug Testing," Journal of Virological Methods, 36:209 (1992), as follows. Blepharitis was scored: 1+, noticeably puffy eyelids; 2+, puffy eyelids with moderate crusting; 3+, eye 50% swollen shut with severe crusting; and 4+, eye totally swollen and crusted shut. Vascularization was scored: 1+, <25% of the cornea involved; 2+, 25–50% involved; and 3+, >50% of the cornea involved. Stromal keratitis was scored: 1+, cloudiness, some iris detail visible; 2+, iris detail obscured; 3+, cornea totally opaque; and 4+, cornea perforated.

Treatment

A 1.0% solution (w/v) was used for treatment. Treatments began four hours post-infection (pi) and consisted of anesthetizing the mice, as described above, placing a 2 µl drop of solution on the cornea, and returning the mouse to its cage. The mice were treated six times per day (equally divided between 9 a.m. and 12 midnight) for the first three days and then four times per day (between 9 a.m. and midnight) for the next four days. One group received extract and the other received buffer (50 mM sodium acetate) only. Scoring was done with the groups masked and the code was broken at the end of the study.

Results: Effect on Blepharitis, Vascularization, and Stromal Keratitis

Blepharitis

On day 4 pi, the blepharitis score in the group treated with the fungal extract (group A) was 1.8. On subsequent days, the severity of blepharitis decreased, to a score of 0.33 on day 13. On day 15, the blepharitis score increased slightly to 0.67, but this was probably due to the variability in the scoring. In the group treated with buffer only (group B), the blepharitis score was 0.9 on day six., the severity of blepharitis increased to a score of 2.2 on day six, and remained between 1.8 and 2.2 from day eight to 11. On day 13, the blepharitis score decreased to 1.4 and continued to decrease to a score of 1.1 on day 15. Statistical analysis of the results on days 11 and 13 showed the differences were significant ($p<0.006$). Blepharitis is the first disease sign to appear, reaching peak severity between days 4–7 and then healing, taking 2–3 weeks to resolve. Thus, treatment with the R. caperata extract appears to primarily enhance the healing of eyelid inflammation. This is similar to other compounds we have tested.

Vascularization

The effect of treatment on the development of corneal neovascularization. In the group given buffer only (group B), vascularization was first noticed on day eight (score 0.22). The extent of blood vessel growth in the cornea then increased in group B to a score of 1.4 on day 11 and continued to increase in severity, reaching a score of 2.7 on day 15. This pattern is typical of this disease sign in KOS-infected mice that have not been treated (Brandt et al., J. Virology Meth. 36:209 (1992)). Vascularization in the treated group (group A) was also first detected on day eight (score 0.44). Vascularization in the treated group increased slightly (0.55) on day 11 and continued to increase after day 11, but at a substantially slower rate than the placebo group (B). On day 15, the vascularization score was 0.8 in group A compared to group B (2.7). Analysis of the results on days 11 through 15 using Student's T-test revealed that the differences were significant ($p<0.05$). Thus, treatment of mice with the mushroom extract significantly reduced the development of corneal neovascularization.

Stromal Keratitis

The effect of treatment on the development of corneal clouding. Stromal keratitis was noticeable on day four in the placebo group (B). Corneal clouding increased in severity at day six (score 0.5) and continued to increase until day 15, when the severity began to plateau. At day 15, the score was 2.7 in group B. A slight amount of corneal clouding was seen in the treated group (A) on day four and remained low through day six. On day eight, the severity of corneal clouding increased to 0.88 and it remained at this level through the end of the experiment on day 15 (score 1.0). Analysis of the results on days 11–15 using Student's T-test revealed that the differences were highly significant (p<0.002). Thus, treatment with the mushroom extract significantly reduced the severity of stromal keratitis.

The results clearly demonstrate that the purified mushroom extract significantly affects the severity of ocular disease caused by HSV-1. Treatment did not appear to prevent the development of blepharitis but did significantly affect the rate of healing. This result is similar to previous work we have done with other compounds and is not surprising since the compound was applied to the cornea and may not have reached effective concentration in the conjunctiva and eyelids.

Stromal keratitis and cornea vascularization both begin between days four and eight and increase in severity thereafter. Treatment with the mushroom extract did not block development of these disease signs but did significantly reduce the severity, indicating a substantial therapeutic effect. One possible explanation for the development of some disease is that we only tested a 1.0% (w/v) solution of the extract. This concentration, on a molar basis, is 16.7 times less than the concentration of the antiviral trifluorothymidine (TFT), the currently used drug for treating HSV-induced ocular infection in the United States, yet we still saw significant reduction in disease.

Example 4

Treatment of HSV-Induced Ocular Infections

Preparation of R. caperata mushroom extract, HSV virus stock, and animal ocular infection with the virus, can be accomplished as described in Example 3. Hypothetically, then, treatment of the ocular infection can be accomplished as described in Example 3, except that an extract concentration of at least 5.0% (w/v) will be used. It is expected that such treatment will prevent the development of HSV-induced ocular disease in the infected animals.

ANALYSIS OF RESULTS

Example 5

Synthesis of 12-Mer/Ubiquitin Compound

Peptide Synthesis

Hypothetically, the 12-mer peptide (SEQ ID NO:1) and ubiquitin (SEQ ID NO:2) components which form the compound of the present invention can be readily synthesized by automated solid phase methods well known to those who are skilled in the art, which methods are set forth in the textbooks *Principles of Peptide Synthesis*, Springer-Verlag, 1984; *Solid Phase Peptide Synthesis*, J. M. Stewart and J. D. Young, Pierce Chemical Company, Rockford, Ill., 1984 (2nd ed.); G. Barany and R. B. Merrifield, *The Peptides*, Ch. 1, pp. 1–285, Academic Press.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide.

Similarly, it is within the skill of the art to use the above-described automated solid phase peptide synthesis to synthesize a peptide having a sequence sufficiently homologous SEQ ID NO:1, to yield a peptide having a correspondingly similar effectiveness to that of the 12-met peptide having that sequence. Similarly, knowing the 76 amino acid sequence of ubiquitin (SEQ ID NO:2), it too can be synthesized using automated solid phase peptide synthesis.

Recombinant DNA Technology

Knowing the amino acid sequence of the novel 12-mer (SEQ ID NO:1), and of ubiquitin (SEQ ID NO:2), it is within the skill of the art to identify and isolate the genes coding for those proteins, and to prepare them by means of recombinant DNA technology, as an alternative to isolating them from R. caperata or preparing each by means of automated solid phase peptide synthesis.

In order to prepare either SEQ ID NO:1 or SEQ ID NO:2 by means of recombinant DNA technology, genes for the peptides must first be created. For peptides of the length of ubiquitin and the 12-mer identified here, it is readily possible to artificially synthesize DNA of proper sequence to encode these peptides. Oligonucleotide synthesis can be used to create DNA segments which can be joined to form an DNA coding sequence for each peptide.

When the gene for each peptide has been made, it can be inserted into a plasmid or vector having suitable flanking regulatory sequences (e.g. promoter) for a desired host. The recombinant plasmid or vector with the inserted gene—the cloned gene—is then introduced, or "transfected", into a host cell. The host cell at that point is "transformed" or "transfected". The vector or plasmid is the carrier which brings the DNA or gene of interest into the host cell, and allows the DNA to grow and replicate as the host cell grows and replicates, eventually causing the host cell to express or produce the peptide.

Peptide effectiveness, whether isolated from R. caperata or produced by means of automated solid phase peptide synthesis or recombinant DNA technology, can be evaluated by means of the in vivo and in vitro procedures described above.

In the above manner, both SEQ ID NO:1 and SEQ ID NO:2, or ubiquitin, can be synthesized. Once the individual peptide sequences are synthesized, the following procedure outlines how SEQ ID NO:1 and SEQ ID NO:2 (ubiquitin), can be covalently linked, resulting in the anti-vital compound of the present invention. K. D. Wilkinson et al, 1988 *Current Communications in Molecular Biology* pp. 19–25. K. D. Wilkinson et al, *Biochemistry* 1986 25:6644–6649.

First, the carboxyl terminus of SEQ ID NO:2 (ubiquitin) is activated. In aqueous solution trypsin is able to cleave ubiquitin at Arg-74 to a 74 amino acid fragment ethyl ester and the corresponding ethyl ester of Des-Gly ubiquitin is formed. Transpeptidation offers an easy route to large amounts of the specific carboxy-terminal derivatives. The reactivity of the ester leaving group is enhanced by hydrazinolysis followed by acyl-azide formation. The ethyl ester is treated with one M hydrazine-HCL at pH 8.0 and 2-C, the acyl hydrazide is formed in quantitative yield with halftime of 70 minutes. After dialysis to remove excess reagents, the acyl hydrazide is converted to the acyl azide by treatment for one minute with 0.5M nitrous acid at −5° C. The resulting acyl azide of ubiquitin is very reactive toward nucleophilic displacement, but is not stable and should be coupled to the nucleophile peptide immediately.

Next to be accomplished is nucleophilic addition of the 12-mer peptide (SEQ ID NO:1) to the activated ubiquitin carboxyl terminus. The 12-mer peptide to be attached to the carboxyl terminus of ubiquitin is cooled in an ice bath and added immediately to the freshly prepared ubiquitin azide at a neutral to basic pH. After two minutes the mixture is dialyzed extensively to remove reagents and the resultant conjugate can be purified from the mixture. The coupling yield is above 50% based on the ubiquitin content and as high as 10% based on the amount of added peptide (added in at least fivefold molar excess of the ubiquitin present).

METHODS OF USE

In the practice of methods to use the compound of the present invention, an effective amount of the 12-mer-ubiquitin compound, synthetic analogue, pharmaceutically acceptable nontoxic salt thereof, or pharmaceutical composition containing same is administered to the subject in need of treatment of viruses having lipid bilayer envelopes, such as Rous sarcoma virus, herpes simplex virus types 1 and 2, varicella zoster, and influenza virus.

Such compounds or compositions may be administered by any of a variety of routes depending upon the specific end use, including orally, intravenously, parenterally (including subcutaneous, intramuscular and intravenous administration), transdermally, nasally, or by suppository..

The most suitable route in any given case will depend upon the use, particular active ingredient, the subject involved, and the judgment of the medical practitioner. The compound or composition may also be administered by means of controlled-release, depot implant or injectable formulations as described more fully here below.

In general for the uses herein above described, it is expected that the active ingredient will be administered in amounts between about 0.001 and 5 mg/kg body weight. Preferably, for human therapy, it is expected that the active ingredient will be administered in the range of from about 0.01 to about 1 mg/kg/day or a 5% topical solution up to 8 times per day. This administration may be accomplished by a single administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parental administration requires lower dosage than other methods of administration (e.g. topical) which are more dependent upon absorption.

PHARMACEUTICAL COMPOSITIONS

A further aspect of the present invention relates to pharmaceutical compositions containing as active ingredients a compound of the present invention which compositions comprise such compound in admixture with a pharmaceutically acceptable, nontoxic carrier. As mentioned above, such compositions may be prepared for use for parental (subcutaneous, intramuscular and intravenous) administration, particularly in the form of liquid solutions or suspensions, for suppositories, for oral administration particularly in the form of tablets or capsules, or intranasally particularly in the form of powders, nasal drops or aerosols.

---

We claim:

1. A substantially pure compound comprising a peptide of SEQ ID NO:1 covalently linked to a peptide of SEQ ID NO:2, or a pharmaceutically acceptable nontoxic salt of the compound.

2. The compound of claim 1 wherein the peptide of SEQ ID NO:1 is linked by an epsilon amino group of its carboxy-terminal lysine residue to the carboxyl terminus of SEQ ID NO:2.

3. A substantially pure compound comprising SEQ ID NO:1 covalently linked to ubiquitin, or a pharmaceutically acceptable nontoxic salt of the compound.

4. A method for inhibiting replication of viruses having lipid bilayer envelopes, the method comprising administering an effective amount of a substantially pure compound comprising SEQ ID NO:1 covalently linked by an epsilon amino group of a carboxy terminal lysine to the carboxyl terminus of SEQ ID NO:2, or a pharmaceutically acceptable nontoxic salt of the compound.

5. A method for inhibiting replication of viruses having lipid bilayer envelopes, the method comprising administering an effective amount of a substantially pure compound comprising SEQ ID NO:1 covalently linked to ubiquitin, or a pharmaceutically acceptable nontoxic salt of the compound.

6. A method for preparing a compound for inhibiting replication of viruses having lipid bilayer envelopes, the method comprising the steps of:

(a) preparing a first biologically pure peptide comprising SEQ ID NO:1;

(b) preparing a second biologically pure peptide comprising SEQ ID NO:2; and (c) covalently linking SEQ ID NO:1 to SEQ ID NO:2.

7. A method for preparing a compound for inhibiting replication of viruses having lipid bilayer envelopes, the method comprising the steps of:

(a) preparing a first biologically pure peptide comprising SEQ ID NO:1;

(b) preparing biologically pure ubiquitin; and (c) covalently linking an epsilon amino group of the carboxy terminal lysine of SEQ ID NO:1 to the carboxyl terminus of ubiquitin.

8. A pharmaceutical composition for inhibiting replication of viruses having lipid bilayer envelopes, comprising as an active ingredient an effective amount of a substantially pure compound comprising SEQ ID NO:1 covalently linked by an epsilon amino group of the carboxy terminal lysine to the carboxyl terminus of SEQ ID NO:2, or a pharmaceutically acceptable nontoxic salt of the compound, in association with a major amount of a nontoxic diluent.

9. A pharmaceutical composition for inhibiting replication of viruses having lipid bilayer envelopes, comprising as an active ingredient an effective amount of a substantially pure compound comprising SEQ ID NO:1 covalently linked to ubiquitin, or a pharmaceutically acceptable nontoxic salt of the compound, in association with a major amount of a nontoxic diluent.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Rozites caperata ( x i ) SEQUENCE DESCRIPTION: SEQ ID NO:1:

Ala Asn Val Val Ala Thr Tyr Pro Ala His Ser Lys
    1                  5                          10

( 2 ) INFORMATION FOR SEQ ID NO:2:

( i ) SEQUENCE CHARACTERISTICS:
        ( A ) LENGTH: 76 amino acids
        ( B ) TYPE: amino acid
        ( C ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Rozites caperata ( x i ) SEQUENCE DESCRIPTION: SEQ ID NO:2:

```
Met Gln Ile Phe Val Lys Thr Leu Thr Gly Lys Thr Ile Thr Leu Glu
1               5                   10                  15
Val Glu Ser Ser Asp Thr Ile Asp Asn Val Lys Ser Lys Ile Gln Asp
                20                  25                  30
Lys Glu Gly Ile Pro Pro Asp Gln Gln Arg Leu Ile Phe Ala Gly Lys
            35              40              45
Gln Leu Glu Gly Arg Thr Leu Ser Asp Tyr Asn Ile Gln Lys Glu Ser
    50              55              60
Thr Leu His Leu Val Leu Arg Leu Arg Arg Gly Gly
65              70              75
```